United States Patent [19]

Fancher

[11] 4,385,922
[45] May 31, 1983

[54] METHOD OF INCREASING THE YIELD OF LEGUMES UTILIZING D- OR DL-α-O,O-DIETHYLPHOSPHORODITHIOYLACETYLPHENYLGLYCINE ETHYL ESTERS

[75] Inventor: Llewellyn W. Fancher, New Castle, Calif.

[73] Assignee: Stauffer Chemical Company, Westport, Conn.

[21] Appl. No.: 296,284

[22] Filed: Aug. 26, 1981

[51] Int. Cl.³ .................. A01N 57/14; C07F 9/165
[52] U.S. Cl. ...................................... 71/87; 260/943
[58] Field of Search .......................... 260/943; 71/87

[56] References Cited
PUBLICATIONS

Berkelhammer et al., "J. Org. Chem.", vol. 26, #7, (1961), pp. 2281–2288.

*Primary Examiner*—Anton H. Sutto
*Attorney, Agent, or Firm*—Michael J. Bradley

[57] ABSTRACT

A method of increasing the yield of legumes (soybeans) utilizing a compound of the formula

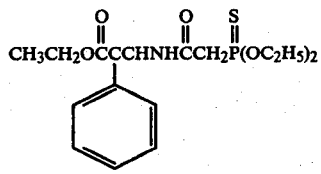

11 Claims, No Drawings

METHOD OF INCREASING THE YIELD OF LEGUMES UTILIZING D- OR DL-α-O,O-DIETHYLPHOSPHORODITHI-OYLACETYLPHENYLGLYCINE ETHYL ESTERS

BACKGROUND OF THE INVENTION

The present invention provides compounds and a method by which the yield of certain plants, particularly crop plants, can be improved by applying to such plants a yield-improving amount of D- or DL-α-O,O-diethylphosphorodithioylacetylphenylglycine ethyl esters, described herein. The plants for which the present invention has been found especialy useful are the legumes, e.g., soybeans, peas, peanuts and clover.

The application of the D or DL-α-O,O-diethylphosphorodithioylacetylphenylglycine ethyl esters improve the yield of legumes as much as about 15 percent. The term "yield" means dry weight of harvested pods of the legume crop plants. The yield per plant and the yield per acre is improved by application of the compound of this invention.

The term "soybean" includes both the determinate type (e.g. Bragg) which is grown in the southern United States, and the indeterminate type (e.g. Corsoy or Williams) which is grown in the northern United States and Canada. Generally, the determinate varieties of soybeans grow very little after flowering, if at all, and branch more profusely than indeterminate varieties. Indeterminate varieties increase their height by two to four times after flowering begins.

DESCRIPTION OF THE INVENTION

The novel compounds that are useful in the practice of this invention are D or DL-α-O,O-diethylphosphorodithioylacetylphenylglycine ethyl esters having the following structural formula

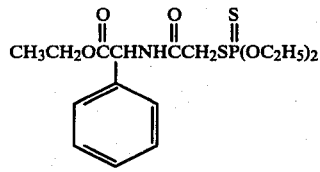

The D sterio isomer has been found to have significantly higher activity than the DL form of the novel compound.

The novel compounds of this invention can be prepared by the following general procedure:

1. Preparation of a phenylglycine ethyl ester

Phenylglycine is suspended in an excess of ethyl alcohol and gaseous hydrogen chloride is passed into the mixture at 25°-65° C. An excess of hydrogen chloride of from 3 to 4-5 times the molar amount of the aminoacid is used. The product, the phenylglycine ethyl ester hydrochloride, can be used directly in step 2 or may optionally be converted to the free ester of reaction with ammonium hydroxide.

2. Preparation of a chloroacetyl phenylglycine ester

The ester prepared in step 1 is reacted with chloroacetylchoride at a temperature of from about −10° to +10° C. in a suitable solvent in the presence of a suitable base to produce chloroacetyl phenylglycine ethyl ester. Solvents useful in this reaction include water, dichloromethane, and dichloroethane. Suitable bases include sodium bicarbonate, sodium carbonate, potassium carbonate, and sodium hydroxide. If the aminoacid is used in the form of its hydrochloride, a two-fold excess of base must be used.

3. Preparation of O,O-dialkylphosphorodithioylaminoacid ester

The chloroacetyl phenylglycine ethyl ester prepared in step 2 is reacted with an O,O-dialkyldithiophosphate or salt thereof at a temperature below 25° C. in a suitable solvent in the presence of a suitable base to produce the corresponding O,O-dialkylphosphonodithioyl phenylglycine ethyl ester. Suitable solvents include tetrahydrofuran, dioxane, dichloromethane and dichloroethane. Suitable bases include triethylamine and pyridine. When the salt form of the dithiophosphate is used in the reaction the organic base is not required.

The following example demonstrates preparation and testing of selected compounds of this invention.

EXAMPLE

Preparation of DL-α-O,O-diethylphosphorodithioylacetylphenylglycine ethyl ester

In a reaction flask, 3.0 grams (g) (0.012 ml) of DL-N-chloroacetyl-α-phenylglycine ethyl ester and 2.5 g (0.014 mole) of O,O-diethyl-dithiophosphonic acid in 50 milliliters (ml) tetrahydrofuran were mixed and cooled to 10° C. in an ice bath. Triethylamine (1.4 g, 0.014 mole) in 10 ml tetrahydrofuran was added slowly at a temperature below 25° C. with cooling. The pH was adjusted to about 7.5 with additional triethylamine and the mixture wa stirred for six hours at room temperature. The solvent was then removed under vacuum and the residue was dissolved in 80 ml of toluene and washed with two 80 ml portions of a saturated salt solution. The toluene solution was then dried over magnesium sulfate, filtered and evaporated to give 4.0 g (84% yield) of solid product having a melting point of 62°-65° C. The product was identified by nuclear magnetic resonance (NMR) spectroscopy as the title compound.

The following is a table of compounds that are useful in the practice of this invention. These compounds are preparable according to the general and specific procedure described herein. Compound numbers are assigned to each compound and are used throughout the remainder of this application.

TABLE I

CH₃CH₂OCCHNHCCH₂SP(OC₂H₅)₂ with O, O, S double bonds and phenyl substituent

| Compound No. | Optic Rotation | $n_D^{30}$ or melting point |
|---|---|---|
| 1 | DL | 62–65° C. |
| 2 | D | 1.5431 |

The structures of these compounds were confirmed by infrared (IR) and/or nuclear magnetic resonance (NMR) spectral analyses.

EVALUATION TEST ON SOYBEANS

The purpose of this test is to evaluate compounds for soybean pod weight increase. Selected compounds of this invention are evaluated for such weight increase in the following manner.

Round fiber pots (6 inches in diameter) are filled with screened, sandy loam soil which has been fortified with 17-17-17 granular fertilizer to yield a soil mix having 150 parts per million (ppm) each of nitrogen, $P_2O_5$ and $K_2O$. Soybean seeds of either the determinate or indeterminate type are planted in the soil about 0.5 inches deep in a single row in sufficient number that 10–15 seedlings are obtained. After the seedlings have reached a unifoliate leaf stage they are thinned to four plants per pot.

Several such pots are retained as controls and other pots are treated with a candidate compound. The time of treatment of the four plants is between an early vegetative state and an early flowering state. The plants are treated with a compound by placing a pot on a linear spray table and spraying with 25 gallons per acre (235 liters per hectare) of an appropriate concentration of chemical compound to yield a treatment of ½, 1 or 2 pounds per acre (lb/A) (35, 70, or 140 grams per hectare). The compounds are dissolved in a 1:1 acetone-$H_2O$ mixture containing 0.5 percent polyoxyethylene sorbitan monolaurate emulsifier prior to the treatment.

The treated plants are placed in a glasshouse and maintained at a temperature of approximately 70° F. at night and 80°–85° F. during the day. The plants are fertilized twice during the crop cycle with 1:1:1 ratio of a nitrogen, $P_2O_5$, $K_2O$ fertilizer solution (3.4 grams nitrogen, $P_2O_5$, $K_2O$ per liter of water). Normally 70 milliliters (ml) of this solution is added to each pot at each of the two fertilization times. Usually these fertilization times are at one and two months after seeding.

Control plants are also fertilized and maintained in the glasshouse in a like manner but are not treated with a candidate compound.

Evaluation is made after the plants have fully matured, i.e., when the leaves and pods have senesced. The term "pods" as used herein means pods with beans. The pods are removed from the treated plants, dried in a forced-air dryer at 120° F. to a constant weight, i.e., until all moisture is evaporated from the pods. Next, the dry weight of the pods is ascertained and compared to the dried weight of pods from an untreated plant.

The percent increase in pod weight is calculated and is reported in Table II.

TABLE II

| Compound Number | Treatment Rate lb/A | Percent Increase in Pod Dry Weight |
| --- | --- | --- |
| 1 | ½ | −8 |
|   | 1 | 8 |
|   | 2 | 5 |
| 2 | ½ | 13 |
|   | 1 | 18 |
|   | 2 | 6 |

Application of the D- or DL-α-O,O-diethylphosphorodithioylacetylphenylglycine ethyl esters of this invention may be made employing the procedures normally used for treatment of plants including dip or soak treatment of tubers, bulbs or cuttings, for example, as well as foliar, bark or stem or soil application. Preferably the compounds are applied in a post-emergence foliar application, more preferably the compounds are applied directly to the plant between about 4 weeks prior to flowering and about 2 weeks after flowering of the plant. Flowers are produced where leaf petioles join the main stem or branches of the main stem. The active ingredient may be utilized in diverse formulations, including the adjuvants and carriers normally employed for facilitating the dispersions of active ingredients for agricultural applications, recognizing the known fact that the formulations and mode of application of a chemical agent may affect its activity in any given application. Thus, D- or DL-α-diethylphosphorodithioylacetyl phenylglycine ethyl esters can be formulated as a solution or dispersion in a non-aqueous medium, as a powdery dust, as a wettable powder, as an emulsifiable concentrate, as a granule or as any of several other known types of formulations, depending upon the desired mode of application. These growth regulatory compositions may be applied as dusts, sprays, dips or granules in the sites in which growth regulation is desired. These formulations may contain as little as 0.0005% or as much as 95% or more by weight of active ingredient and applications may be at rates of about 1/32 to about 5 pounds per acre, preferably about 1/16 to about 2 pounds per acre.

Dusts are admixtures of the active ingredient with finely divided solids such as talc, attapulgite clay, kieselguhr and other organic and inorganic solids which act as dispersants and carriers for the regulant. These finely divided solids have an average particle size of less than 50 microns. A typical dust formulation useful herein is one containing 1.0 part of D- or DL-α-diethylphosphorodithioylacetyl phenylglycine ethyl ester and 99.0 parts of talc.

Wettable powders are in the form of finely divided particles which disperse readily in water or other dispersant. The wettable powder is ultimately applied to the plant either as a dry dust or as an emulsion in water or other liquid. Typical carriers for wettable powders include fuller's earth, kaolin clays, silicas, and other highly absorbent, wettable inorganic diluents. Wettable powders normally are prepared to contain about 5% to 80% of active ingredient, depending upon the absorbency of the carrier and usually also contain a small amount of a wetting, dispersing or emulsifying agent to facilitate dispersion.

Other useful formulations for plant applications are the emulsifiable concentrates which are homogeneous liquid or paste compositions which are dispersable in water or other dispersant and may consist entirely of D- or DL-α-O,O-diethylphosphorodithioylacetyl phenylglycine ethyl ester with a liquid or solid or emulsifying agent or may also contain a liquid carrier such as xylene, heavy aromatic naphthas, isophorone and other non-volatile organic solvents. For plant application, these concentrations are dispersed in water or other liquid carrier and normally applied as a spray to the area to be treated. The percentage of weight of the essential active ingredient may vary according to the manner in which the composition is to be applied, but in general, comprises 0.005% to 95% of active ingredient.

Other useful formulations include simple solutions of the active ingredient in a dispersant in which it is completely soluble at the desired concentration, such as acetone or other organic solvents. Granular formulations wherein the chemical agent is carried on relatively coarse particles are of particular utility for aerial distribution or for penetration of cover crop canopy. Pressurized sprays, typically aerosols wherein the active ingredient is dispersed in finely-divided form as a result of vaporization of low boiling dispersant solvent carrier such as the freons, may also be used.

Of course, the formulations, concentration and mode of application of D- or DL-α-O,O-diethylphosphorodithioylacetyl phenylglycine ethyl esters will be adapted to the particular plant and surrounding circumstances as is the case in all agronomic applications.

The active growth regulatory compound of this invention may be formulated and/or applied with other agricultural chemicals, such as insecticides, fungicides, nematocides, fertilizers and the like. In addition, combinations of D- or DL-α-O,O-diethylphosphorodithioylacetyl phenylglycine ethyl esters with certain plant hormones, such as native auxins, anti-auxins, giberellins and kinins, may produce enhanced growth regulatory effects.

What is claimed is:

1. D-α-O,O-diethylphosphorodithioylacetylphenylglycine ethyl ester.
2. DL-α-O,O-diethylphosphorodithioylacetylphenylglycine ethyl ester.
3. A composition of matter comprising
   (a) a growth regulating amount of D-α-O,O-diethylphosphorodithioylacetylphenylglycine ethyl ester; and
   (b) an inert carrier.
4. A composition of matter comprising
   (a) a growth regulating amount of DL-α-O,O-diethylphosphorodithioylacetylphenylglycine ethyl ester; and
   (b) an inert carrier.
5. A method of increasing the yield of legumes comprising applying thereto a yield-increasing amount of D-α-O,O-diethylphosphorodithioylacetylphenylglycine ethyl ester.
6. A method of increasing the yield of legumes comprising applying thereof a yield-increasing amount of DL-α-O,O-diethylphosphorodithioylacetylphenylglycine ethyl ester.
7. The method of claim 5 wherein the legume is soybeans.
8. The method of claim 6 wherein the legume is soybeans.
9. The method of claims 7 or 8 wherein the yield-increasing amount of said compound is between about 1/32 to about 5 pounds per acre.
10. The method of claims 7 or 8 wherein the yield-increasing amount is applied between about 4 weeks prior to flowering of the soybeans plant and 2 weeks after said flowering.
11. The method of claims 7 or 8 wherein the yield-increasing amount of said compound is between about 1/16 to about 2 pounds per acre.

* * * * *